United States Patent [19]

Koenig

[11] Patent Number: 4,734,405

[45] Date of Patent: Mar. 29, 1988

[54] COMBINATION PRODUCT

[75] Inventor: Horst Koenig, Ludwigshafen, Fed. Rep. of Germany

[73] Assignee: BASF Aktiengesellschaft, Ludwigshafen, Fed. Rep. of Germany

[21] Appl. No.: 917,175

[22] Filed: Oct. 9, 1986

[30] Foreign Application Priority Data

Oct. 9, 1985 [DE] Fed. Rep. of Germany ....... 3535947

[51] Int. Cl.$^4$ ............................................. A61K 31/62
[52] U.S. Cl. .................................................... 514/161
[58] Field of Search ......................................... 514/161

[56] References Cited

U.S. PATENT DOCUMENTS 4,258,185  3/1981  Nakao et al. .......................... 544/114
4,636,504  1/1987  Rossy et al. .......................... 514/252

OTHER PUBLICATIONS

Mills et al., Platelets & Thrombosis, Proceedings of the Serono Symposia, vol. 10, 1977, pp. 175–179.
Liste Pharmindex III/84, Colfarit®.

Primary Examiner—Stanley J. Friedman
Attorney, Agent, or Firm—Keil & Weinkauf

[57] ABSTRACT

A combination of acetylsalicylic acid and pyridazinone derivatives can be used for the treatment of thromboembolic disorders.

3 Claims, No Drawings

COMBINATION PRODUCT

The present invention relates to a novel combination product for the treatment of thromboembolic disturbances of blood flow.

It is known (cf. German Laid-Open Applications DOS No. 2,845,220 and DOS No. 3,124,699 and European Laid-Open Application No. 117,403) that certain pyridiazinone derivatives have a platelet aggregation-inhibiting action. It is also known that, because of its platelet aggregation-inhibition action, acetylsalicylic acid is used for the prophylaxis of thromboembolic disorders (cf. Liste Pharmindex III/84, Colfarit(®)).

We have found that the activity of acetylsalicylic acid can be greatly increased by pyridazinone derivatives.

The present invention relates to a drug which contains acetylsalicylic acid and a pyridazinone derivative of the formula I

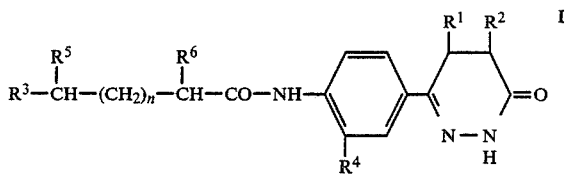

where $R^1$ is hydrogen or methyl, $R^2$ is hydrogen or, together with $R^1$, forms methylene or ethylene, $R^3$ is (a) a group of the formula

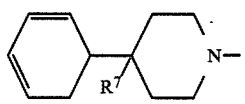

where the dashed line may be an additional bond and, where relevant, $R^7$ is hydrogen or $C_1$-$C_4$-acyl, or (b) a group of the formula

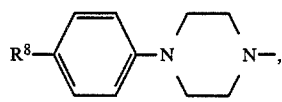

where $R^8$ is hydrogen or $C_1$-$C_4$-acyl, or (c) 1,3-tetrahydroisoquinolin-2-yl, $R^4$ is hydrogen or, together with $R^3$, forms a direct bond or methylene, $R^5$ is hydrogen or methyl, $R^6$ is hydrogen or halogen and n is 0 or 1, acetylsalicylic acid being present in an amount of 100–600 parts by weight and the compound I in an amount of 5–50 parts by weight.

The acetylsalicylic acid may be incorporated into the drug also in the form of its physiologically tolerated salts. Particularly suitable salts are the alkali metal and alkaline earth metal salts.

The stated mixing ratio is based on free acetylsalicylic acid, the preferred mixing ratio being about 300 parts of acetylsalicylic acid to 10 parts of compound I.

The superior action of the novel combination can be demonstrated by determining the platelet aggregation in the following experiments:

1. Platelet-rich plasma is obtained from venous citrated blood by centrifuging (300 g, 10 minutes duration at 4° C.). Photometric measurement of platelet aggregation is carried out with the addition of $MgCl_2$ (final concentration 10 mmol/l) and collagen Stago (final concentration 0.02 mg/ml), in an Mk 3 Born aggregometer. The maximum change in extinction per second is used as a measure of aggregation.

Testing of the aggregation-inhibiting activity of the substances is carried out after an incubation time of 10 minutes.

The concentration which causes a 50% inhibition of aggregation is determined as the EC 50%.

The substances and the combination are administered orally to beagles weighing from 10 to 15 kg. Before, as well as 2 and 4 hours after, administration of the substance, venous blood is withdrawn and rendered incoagulable by adding citrate, after which platelet-rich plasma is obtained from this blood by centrifuging (300 g, 10 minutes duration at 4° C.). The addition of adrenalin (final concentration $5 \times 10^{-8}$ mol/l) and collagen (final concentration $2 \times 10^{-3}$ g/l) to platelet-rich plasma induces aggregation, which is measured as extinction in the Mk 3 Born aggregometer. The maximum change in extinction per second is used as a measure of aggregation. The percentage inhibition of aggregation was determined by comparing the values before and after administration of the substance.

In Experiment 2, the following results were obtained:

| Substance | Dose (mg/kg) | Inhibition of aggregation (%) |
|---|---|---|
| Amipizone (European Laid-Open Application 117,403, Example 13) | 0.1 | 10 |
| Acetylsalicylic acid | 1.0 | 0 |
| Amipizone + acetylsalicylic acid | 0.1 + 1.0 | 16 |

The novel combination is useful for the treatment and prophylaxis of disorders caused by platelet aggregation. These include thromboembolic disorders of the heart, brain and the peripheral, arterial vascular system. Examples of such disorders are cardiac infarction, strokes and obliterative arteriosclerosis.

The novel combination is furthermore useful for the treatment and prophylaxis of disorders caused by the release of vasoactive substances from aggregating platelets, for example migraine, vasospastic angina and Raynaud's disease. It is also useful for preventing complications during surgical measures, such as vascular prostheses and shunts.

The combination according to the invention can be administered orally in a conventional manner.

The dosage depends on the age, condition and weight of the patient and on the route of administration. As a rule, the daily dose is from about 5 to 50 mg, preferably about 10 mg, of compound I and from about 30 to 600 mg, preferably about 300 mg, of acetylsalicylic acid per patient.

The novel combination can be employed in the conventional solid or liquid pharmaceutical forms, such as tablets, film tablets, capsules, powders, granules, coated tablets, pellets, controlled release pellets or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retardants and/or antioxidants (cf. H.

Sucker et al., Pharmazeutische Technologie, Thieme-Verlag, Stuttgart, 1978). The administration forms thus obtained normally contain from 10 to 99% by weight of the active compound.

EXAMPLE 1

Tablets having the following composition were pressed on a tablet press in a conventional manner:
300 mg of acetylsalicylic acid
5 mg of 2-(1,2,3,4-tetrahydroquinolin-2-on-6-yl)-3,4-diazabicyclo[4.1.0]hept-2-en-5-one
72 mg of corn starch
13 mg of gelatin
35 mg of lactose
25 mg of carboxymethylcellulose
17.5 mg of talc
3.5 mg of magnesium stearate

EXAMPLE 2

Tablet cores having the following composition were prepared in a conventional manner:
200 mg of acetylsalicylic acid
5 mg of 2-(2,3,4,5-tetrahydrobenzo[b]azepin-2-(1H)-on-7-yl)-3,4-diazabicyclo[4.2.0]oct-2-en-5-one
100 mg of core material.

The core material consisted of 9 parts of corn starch, 3 parts of lactose and 1 part of ®Luviskol VA 64 (60:40 vinylpyrrolidone/vinyl acetate copolymer, cf. Pharm. Ind. 1962, 586). The sugar-coating material consisted of 5 parts of sucrose, 2 parts of corn starch, 2 parts of calcium carbonate and 1 part of talc.

The cores obtained were then coated with the sugar-coating material of the above composition.

EXAMPLE 3

To produce film-coated tablets, the tablet cores prepared as described in Example 2 were coated with a film coating having the following composition:

| Tylose | 0.7% | Corn starch | 2.0% |
| --- | --- | --- | --- |
| ® Kollidon 25 (PVP) | 0.4% | Calcium carbonate | 3.5% |
| Sucrose | 70.0% | Gum arabic | 2.5% |
| Finely divided silica | 1.4% | Titanium dioxide | |
| Talc | 11.0% | +colorants | 8.5% |

EXAMPLE 4

Controlled release pellets suitable for introducing into hard gelatin capsules were prepared, each component being pelletized separately and the controlled release pellets then being introduced into the capsules either in the form of a mixture or in succession.
Composition of the pellets per dose:
Controlled release pellets, compound I:
400 mg of acetylsalicylic acid
60 mg of cellulose powder
5 mg of corn starch
10 mg of talc
35 mg of ethylcellulose
Controlled release pellets, compound II:
5 mg of 6-[p-3-(4-phenyl-1-piperidyl)-propionylaminophenyl]-4,5-dihydro-5-methyl-3(2H)-pyridazinone
20 mg of cellulose powder
10 mg of corn starch
10 mg of ethylcellulose

EXAMPLE 5

Pellets suitable for introducing into hard gelatin capsules were prepared, the pellets having the following composition:
300 mg of acetylsalicylic acid
10 mg of 6-[p-3-(4-phenyl-1-piperazinyl)-propionylaminophenyl]-4,5-dihydro-5-methyl-3(2H)-pyridazinone
80 mg of cellulose powder
30 mg of corn starch
5 mg of ®Kollidon 30 (PVP)
20 mg of (®)Eudragit S (polymer of methacrylic acid and methacrylate)
15 mg of talc.

I claim:
1. An orally administrable pharmaceutical composition for treating and preventing disorders caused by platelet aggregation which comprises acetylsalicylic acid and a pyridazinone derivative of the formula I

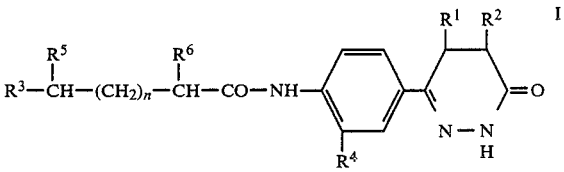

where $R^1$ is hydrogen or methyl, $R^2$ is hydrogen or, together with $R^1$, forms methylene or ethylene, $R^3$ is
(a) a group of the formula

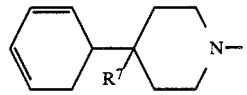

where the dashed line may be an additional bond and, where relevant, $R^7$ is hydrogen or $C_1$-$C_4$-acyl, or
(b) a group of the formula

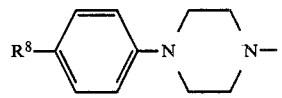

where $R^8$ is hydrogen or $C_1$-$C_4$-acyl, or
(c) 1,3-tetrahydroisoquinolin-2-yl, $R^4$ is hydrogen or, together with $R^3$, forms a direct bond or methylene, $R^5$ is hydrogen or methyl, $R^6$ is hydrogen or halogen and n is 0 or 1, acetylsalicylic acid being present in an amount of 30–600 parts by weight and the compound I in an amount of 5–50 parts by weight.

2. A process for the treatment and prophylaxis of disorders caused by platelet aggregation which comprises: orally administering to a patient to be treated an effective amount of a composition as defined in claim 1.

3. A composition as defined in claim 1, wherein the pyridiazinone derivative is selected from the group consisting of 2-(1,2,3,4-tetrahydroquinolin-2-on-6-yl)-3,4-diazabicyclo[4.1.0]-hept-2-en-5-one, 2-(2,3,4,5-tetrahydrobenzo[b]azepin-2-(1H)-on-7-yl)-3,4-diazabicyclo[4.2.0]oct-2-en-5-one, 6-[p-3-(4-phenyl-1-piperidyl)-propionylamino-phenyl]-4,5-dihydro-5-methyl-3(2H)-pyridazinone and 6-[p-3-(4-phenyl-1-piperazinyl)-propionylaminophenyl]-4,5-dihydro-5-methyl-3(2H)-pyridazinone.

* * * * *